United States Patent [19]

Marxhausen

[11] Patent Number: 4,959,879

[45] Date of Patent: Oct. 2, 1990

[54] METHOD OF AESTHETICALLY DISGUISING A PILLOW

[76] Inventor: Joanne G. Marxhausen, 1530 Concordia, Irvine, Calif. 92715

[21] Appl. No.: 360,139

[22] Filed: Jun. 1, 1989

[51] Int. Cl.⁵ .......................... A47G 9/00; A63H 3/00
[52] U.S. Cl. ......................................... 5/434; 5/482; 5/490; 446/73
[58] Field of Search ................... 5/434, 437, 482, 490, 5/491; 446/73, 369; 428/79, 919; D6/597–601

[56] References Cited

U.S. PATENT DOCUMENTS

| | | | |
|---|---|---|---|
| D. 171,536 | 2/1954 | Flanagin | D6/598 |
| D. 256,414 | 8/1980 | Rich . | |
| D. 269,575 | 7/1983 | Fogarty et al. . | |
| 690,914 | 1/1902 | Bentley | 5/490 |
| 1,754,937 | 4/1930 | Comstock | D6/597 X |
| 2,347,405 | 4/1944 | Ford | 446/369 |
| 2,961,668 | 11/1960 | Hayes . | |
| 3,992,733 | 11/1976 | Racine | 5/437 |
| 4,091,481 | 5/1978 | Redman . | |
| 4,197,604 | 4/1980 | Nakamura . | |
| 4,607,674 | 8/1986 | Noble | 428/919 X |

Primary Examiner—Michael F. Trettel
Attorney, Agent, or Firm—Leon Gilden

[57] ABSTRACT

A method for disguising a pillow is presented including utilizing a flexible sheath formed with a lower closed end and an upper open end. The sheath has secured thereto a series of upper and lower appendages and a facial or visage group to present a masking appearance of an associated pillow "P". The pillow is inserted within the sheath, and the upper end of the sheath gathered and secured by use of a securement collar. The securement collar is formed with lace-like trim at an upper edge thereof with orthogonally and upwardly extending filament members to disguise the upper end of the sheath subsequent to securement of the collar about the upper end.

4 Claims, 1 Drawing Sheet

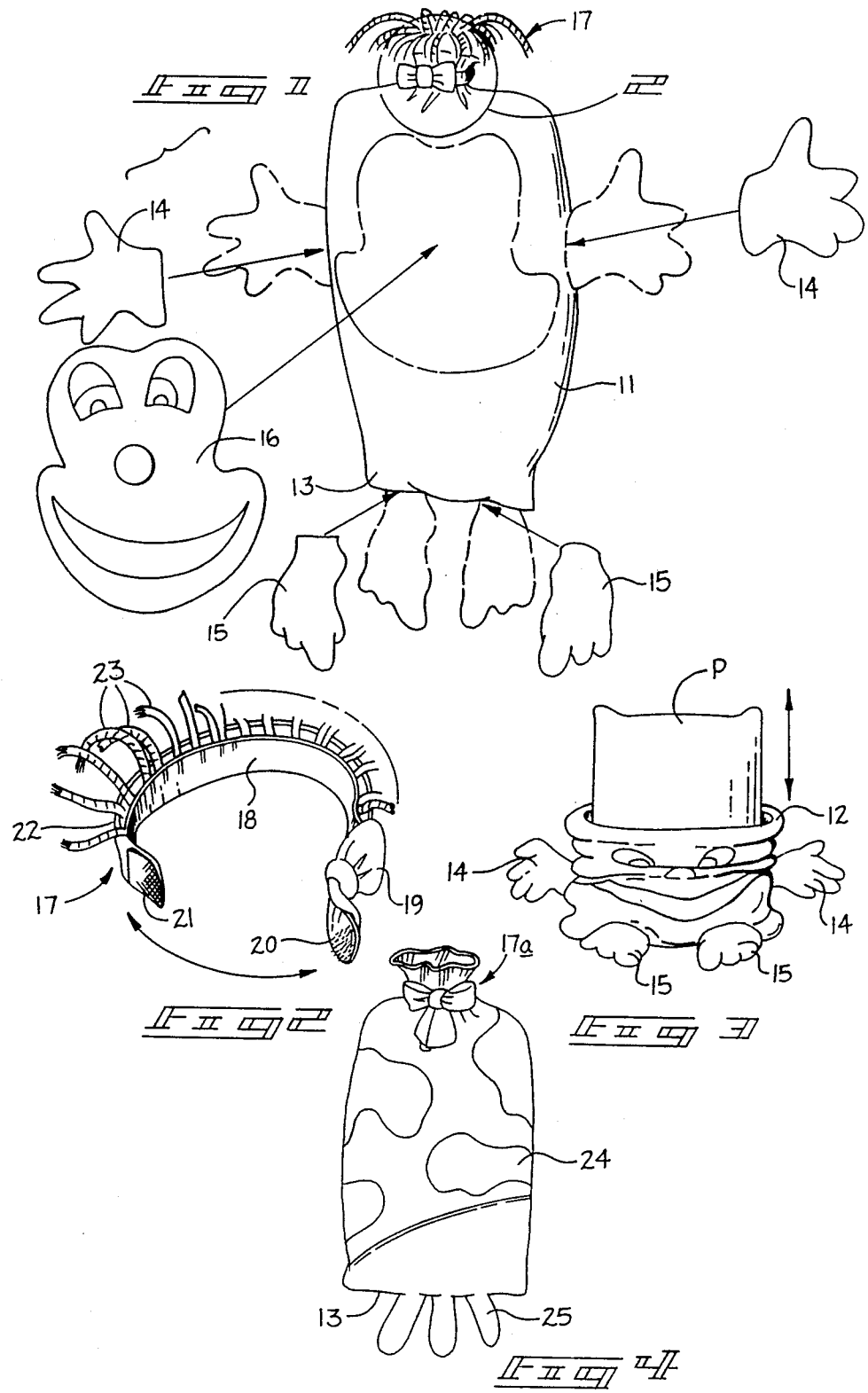

METHOD OF AESTHETICALLY DISGUISING A PILLOW

BACKGROUND OF THE INVENTION

1. Field of the Invention

The field of invention relates to fanciful organizations, and more particularly pertains to a new and improved method of aesthetically disguising a pillow for display within a living environment.

2. Description of the Prior Art

The use of decorative pillows is well known in the prior art. However, heretofore the prior art has not presented an effective means of disguising pillows within a living environment where storage space is at a minimum. The instant invention attempts to overcome the deficiencies of the prior art by enabling exposed and visual display of pillows during storage thereof by positioning such pillows within a fanciful covering. Examples of the prior art include U.S. Pat. No. 2,961,686 to Hayes wherein a series of arm and body portions are secured together to form a slumber pillow for encircling a child and the like utilizing such an organization.

U.S. Pat. No. 4,091,481 to Redman sets forth a pillowshaped three-dimensional tooth-like organization with a tooth and corner receiving pocket for a fanciful exchange of a tooth for a coin in a child's imaginative period.

U.S. Pat. No. 4,197,604 to Nakamura sets forth a pillow provided with arms and finger-like projections to enable the pillow t o form a closed loop in a closed mode utilization of the pillow.

U.S. Pat. No. 256,414 to Rich and U.S. Pat. No. 269,575 to Fogarty illustrate ornamental pillows of conventional construction, as is typical of the prior art, to provide an ornamental casing with appropriate padding therein, as opposed to the instant invention utilizing a pillow secured within a disguising sheath.

As such, it may be appreciated that there is a continuing need for a new and improved method of aesthetically disguising a pillow which addresses both the problems of storage and aesthetic appearance of such storage and in this respect, the present invention substantially fulfills this need.

SUMMARY OF THE INVENTION

In view of the foregoing disadvantages inherent in the known types of decorative pillows now present in the prior art, the present invention provides a method of aesthetically disguising a pillow wherein the same provides for a sheath having secured thereto a series of aesthetic features for receiving a unitary pillow within the sheath and subsequently utilizing a disguising securement collar about an upper open end of the sheath for containing the pillow. As such, the general purpose of the present invention, which will be described subsequently in greater detail, is to provide a new and improved method of aesthetically disguising a pillow which has all the advantages of the prior art decorative pillow organizations and none of the disadvantages.

To attain this, the present invention comprises a method of aesthetically disguising a pillow including the steps of providing a flexible sheath formed with an open upper end and a closed lower end. The sheath has secured thereto utilizing adhesives or a sewing technique to secure a series of upper and lower appendages to the sheath wherein the upper appendages are secured to elongate sides of the sheath with the appendages aligned within and opposed to one another with the lower appendages secured to the lower end of the sheath. A visage or facial group is adhesively or sewingly secured to an exterior surface of the sheath between the upper appendages comprising items including eyes, a nose, and a mouth. The pillow is inserted within the sheath through the upper end wherein the upper end is then gathered together with a securement collar fixedly secured about the open upper end with the securement collar formed to mask the open upper end and enhance the overall appearance of the sheath to disguise the storage of the pillow therein.

My invention resides not in any on of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved method of aesthetically disguising a pillow which has all the advantages of the prior art pillow organizations and none of the disadvantages.

It is another object of the present invention to provide a new and improved method or aesthetically disguising a pillow which may be easily and efficiently manufactured and marketed.

It is a further object of the present invention to provide a new and improved method of aesthetically disguising a pillow which is of a durable and reliable construction.

An even further object of the present invention is to provide a new and improved method of aesthetically disguising a pillow which is susceptible of a low cost of manufacture with regard to both materials and labor, and which accordingly is then susceptible of low prices of sale to the consuming public, thereby making such methods of aesthetically disguising a pillow economically available to the buying public.

Still yet another object of the present invention is to provide a new and improved method of aesthetically disguising a pillow which provides in the apparatuses and methods of the prior art some of the advantages thereof, while simultaneously overcoming some of the disadvantages normally associated therewith.

Still another object of the present invention is to provide a new and improved method of aesthetically disguising a pillow wherein a pillow is inserted within a sheath having secured thereto various adornments thereon to mask the true storage nature of the enclosed pillow within the sheath.

These together with other objects of the invention, with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of the instant invention.

FIG. 2 is an isometric illustration of the securement collar as indicated in section 2 of FIG. 1.

FIG. 3 is an isometric illustration depicting the insertion of a pillow within the associated sheath.

FIG. 4 is an isometric illustration of a modification of the instant invention.

DESCRIPTION OF THE PREFERRED EMBODIMENT

With reference now to the drawings, and in particular to FIGS. 1 to 4 thereof, a new and improved method of aesthetically disguising a pillow embodying the principles and concepts of the present invention and generally designated by the reference numeral 10 will be described.

More specifically, the method of aesthetically disguising a pillow 10 essentially comprises the steps of providing an elongate flexible sheath 11 formed of an interwoven fabric or continuously formed polymeric material. The sheath 11 is formed with an open upper end 12 parallel to and spaced above a closed lower end 13 to provide a storage interior therewithin. The sheath has secured thereto a plurality of upper appendages 14 secured to side surfaces of the sheath, wherein the appendages are generally aligned relative to one another and positioned on opposed sides of the sheath with lower appendages is secured to the closed lower end 13 of the sheath. Subsequently, a visage group 16 comprising eyes, nose, a mouth, and other accessory configurations are secured to an exterior surface of the sheath between the upper appendages 14 and generally symmetrically positioned between the upper appendages. The sheath 11 is then collapsed, as illustrated in FIG. 3, with the pillow "P" inserted within the interior of the sheath whereupon the sheath is pulled up over the pillow "P" with the open upper and 12 gathered together. A securement collar 17 is secured about the open upper end to contain the pillow "P" within the now enclosed sheath. The securement collar 17 is formed as a flexible, discontinuous band 18 provided with an overlay 19 secured about a first terminal end of the band wherein the overlay includes a first hook and loop fastener patch 20 secured to an interior surface of the overlay 19 cooperative with a second hook and loop fastener patch 21 secured to a second terminal end of the flexible band 18. The hook and loop fasteners are secured together to secure the pillow "P" within the sheath, as noted. The band is further formed with a lace strip 22 with orthogonally and upwardly extending filament members 28 extending above and beyond the upper edge of the band and is of a length to extend beyond the open upper end of the sheath to mask that end of the sheath when the securement band 17 is secured to the gathered open upper end adjacent the upper end of the sheath.

FIG. 4 is illustrative of a modification utilizing patterned layers 24 secured to the exterior surface with a series of lower appendages 25 secured to the lower end 13 of the sheath as a variation of masking the enclosed pillow.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A method of aesthetically disguising a pillow comprising the steps of, providing an elongate, flexible sheath and forming the sheath with an upper terminal end and a closed lower terminal end, and securing plural groups of attachments to an exterior surface of the sheath to disguise the appearance of the sheath, and inserting a single, continuous pillow within the sheath, and subsequently gathering the open upper end of the sheath together, and providing a flexible band, and securing the flexible band to the gathered upper end of the sheath adjacent the upper terminal end of the sheath, and wherein the step of securing plural groups of attachments to the exterior surface of the sheath further includes the step of securing a plurality of lower appendages to the lower end of the sheath and securing a plurality of upper appendages to a side surface of the sheath and further securing the upper appendages aligned with one another and on opposed sides of the sheath.

2. A method of aesthetically disguising a pillow as set forth in claim 1 further providing a visage group including a nose, a mouth, and a plurality of eyes and securing the visage group to an exterior surface of the sheath between the upper appendages, and positioning the visage group symmetrically between the upper appendages prior to their securement to the sheath.

3. A method of aesthetically disguising a pillow as set forth in claim 2 wherein the step of providing a flexible band includes forming the flexible band as a discontinuous flexible member, and securing an overlay over and beyond a first terminal end of the band, and providing a first hook and loop fastener patch to an interior surface of the overlay, and providing a second hook and loop fastener patch to an exterior second end of the band to enable securement of the first hook and loop fastener patch to the second hook and loop fastener patch, and further providing a lace trim to an upper edge of &he band and further securing a series of filaments to an upper edge of the band extending beyond the upper edge of the band, and forming the filaments of a length to extend beyond the terminal upper end of the sheath when the band is secured to the sheath.

4. A method of aesthetically disguising a pillow as set forth in claim 3 wherein the step of inserting the pillow within the sheath includes the step of collapsing the sheath and subsequently positioning the pillow within the sheath and thereafter extending the sheath above and beyond the pillow to enclose a pillow therein.

* * * * *